United States Patent [19]

Algieri et al.

[11] 4,282,363
[45] Aug. 4, 1981

[54] 1-NITRO-2-(2-ALKYNYLAMINO)-2-[(2-PYRIDYLMETHYLTHIO)-ETHYLAMINO]ETHYLENE DERIVATIVES

[75] Inventors: Aldo A. Algieri, Fayetteville; Ronnie R. Crenshaw, Dewitt, both of N.Y.

[73] Assignee: Bristol-Myers Company, New York, N.Y.

[21] Appl. No.: 129,157

[22] Filed: Mar. 10, 1980

Related U.S. Application Data

[62] Division of Ser. No. 963,477, Nov. 24, 1978, abandoned.

[51] Int. Cl.³ .......................................... C07D 213/38
[52] U.S. Cl. .................................. 546/332; 546/286; 546/306; 546/300; 424/263
[58] Field of Search ............... 546/286, 300, 332, 306

[56] References Cited

U.S. PATENT DOCUMENTS

| | | | |
|---|---|---|---|
| 3,953,460 | 4/1976 | Durant et al. | 546/300 |
| 4,060,621 | 11/1977 | Durant et al. | 424/263 |
| 4,098,898 | 7/1978 | Durant et al. | 546/332 |
| 4,112,234 | 9/1978 | Crenshaw et al. | 548/342 |
| 4,200,760 | 4/1980 | Algieri et al. | 548/342 |
| 4,203,909 | 5/1980 | Algieri et al. | 260/347.2 |

FOREIGN PATENT DOCUMENTS

| | | | |
|---|---|---|---|
| 844504 | 7/1975 | Belgium | 548/342 |
| 841814 | 11/1976 | Belgium | 548/342 |
| 857388 | 2/1978 | Belgium | 548/342 |
| 1421792 | 1/1976 | United Kingdom | 548/342 |

OTHER PUBLICATIONS

Ganellin et al., Federation Proceedings, vol. 35, pp. 1924–1930, (1976).
Drugs of the Future, vol. I, No. I, (1976).

*Primary Examiner*—Alan L. Rotman
*Attorney, Agent, or Firm*—Richard R. Lloyd

[57] ABSTRACT

Compounds of the formula

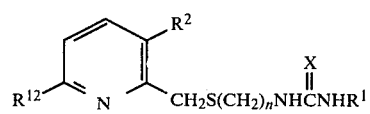

wherein $R^1$ is a straight or branched chain alkynyl group containing from 3 to 9 carbon atoms, inclusive; $R^2$ is hydrogen, hydroxy, cyano, (lower)alkyl, (lower)alkoxy, halogen or amino; n is 2 or 3; X is $NR^3$ or $CHR^3$; $R^3$ is cyano, nitro, $SO_2Ar$; or $SO_2(lower)alkyl$; $R^{12}$ is hydrogen or $(CH_2)_pNR^{13}R^{14}$; p is an integer of from 1 to 4, inclusive; $R^{13}$ and $R^{14}$ each are independently hydrogen or (lower)alkyl; and Ar is phenyl or phenyl containing 1 or 2 substituents independently selected from halogen and (lower)alkyl; and nontoxic, pharmaceutically acceptable salts thereof, are potent anti-ulcer agents.

8 Claims, No Drawings

1-NITRO-2-(2-ALKYNYLAMINO)-2-[(2-PYRIDYL-METHYLTHIO)-ETHYLAMINO]ETHYLENE DERIVATIVES

REFERENCE TO RELATED APPLICATION

This application is a divisional of our earlier, co-pending application Ser. No. 963,477, filed Nov. 24, 1978.

SUMMARY OF THE INVENTION

This application relates to certain N-alkynyl-N'-{ω-[(3- and 6- optionally substituted-2-pyridyl)methylthio]alkyl}-derivatives of N''-cyanoguanidine and of 1,1-diamino-2-substituted ethylene, which are histamine $H_2$-receptor blocking agents, which inhibit gastric secretion and which are useful in the treatment of ulcers, and to processes for their preparation.

BACKGROUND AND PRIOR ART

The clinical objective in treatment of peptic ulcer disease is to decrease gastric acid secretion, based on the principle "no acid, no ulcer." Traditional peptic ulcer disease therapy involves control of diet and the use of antacids and anticholinergics.

There is evidence indicating that histamine may be the final common pathway for stimulation of gastric secretion. This effect of histamine is mediated via $H_2$-receptors and is not inhibited by the classical antihistamines, which are $H_1$-receptor blockers. A number of specific $H_2$-receptor blocking agents ($H_2$-receptor antagonists) are now known. These compounds inhibit basal acid secretion, as well as secretion by other known gastric acid stimulants, and are useful in the treatment of peptic ulcers.

Burimamide (IIa) was the first clinically effective $H_2$-receptor antagonist. It inhibits gastric secretion in animals and man, but oral absorption is poor.

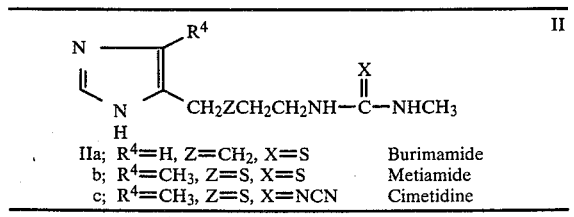

| | | |
|---|---|---|
| IIa; $R^4$=H, Z=$CH_2$, X=S | | Burimamide |
| b; $R^4$=$CH_3$, Z=S, X=S | | Metiamide |
| c; $R^4$=$CH_3$, Z=S, X=NCN | | Cimetidine |

Metiamide (IIb), a subsequently evaluated $H_2$ antagonist, is more potent than burimamide and is orally active in man. Clinical utility was limited, however, owing to toxicity (agranulocytosis). Cimetidine (IIc) is as effective an $H_2$ antagonist as metiamide, without producing agranulocytosis, and has recently been marketed as an anti-ulcer drug. The half-life of cimetidine is relatively short, thereby necessitating a therapeutic regimen of multi daily doses of 200-300 mg. tablets. There is thus a need for anti-ulcer agents which are longer acting and/or more potent than cimetidine.

Reviews on the development of $H_2$ antagonists, including those discussed in the preceding paragraph, may be found in C. R. Ganellin, et al., Federation Proceedings, 35, 1924 (1976), in Drugs of the Future, 1, 13 (1976), and in references cited therein. Relevant patents are as follows:

Belgian Pat. No. 841,814 (Farmdoc 90568X) discloses inhibitors of histamine-stimulated gastric secretion having the formula

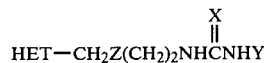

in which HET is one of eight named heterocyclic rings (including pyridyl) which may be substituted by (lower)alkyl, hydroxyl, amino or halogen; Z is sulfur or $CH_2$; X is S, $CHNO_2$, NCN or NH; Y is $NH_2$, (lower)alkylamino, di(lower)alkylamino, (lower)alkoxy, phenylethyl, imidazolylethyl, allyl, trifluoroethyl or $(CH_2)_nR$; n is 1-12; and R is OH, (lower)alkoxy, $NH_2$ or (lower)alkylamino; provided that, when X is NH, Y is trifluoroethyl or $(CH_2)_nR$; and when X is NCN, Y may not be amino or (lower)alkylamino.

Belgian Pat. No. 804,144 (Farmdoc 19437V) discloses inhibitors of histamine-stimulated gastric acid secretion having the formula

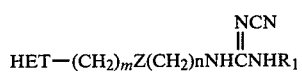

in which HET is a 5 or 6 membered heterocyclic ring containing nitrogen (pyridine is named), which may be substituted by alkyl, halogen, $CF_3$, OH or $NH_2$; m and n are each 0-4 and the sum of m and n is from 2 to 4; Z is sulfur, oxygen, NH or $CH_2$; and $R_1$ is hydrogen or (lower)alkyl.

U.K. Pat. No. 1,421,792 discloses $H_2$-receptor inhibitors of the formula

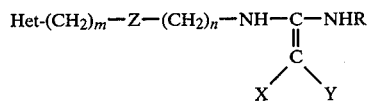

wherein X and Y, which may be the same or different, are hydrogen, nitro, cyano or $SO_2Ar$, but may not both be hydrogen; R is hydrogen, (lower)alkyl or Het$(CH_2)_mZ(CH_2)_n$; Z is sulfur or methylene; m is 0, 1 or 2 and n is 2 or 3 provided that the sum of m and n is 3 or 4; Het is an imidazole, pyridine, thiazole, isothiazole, oxazole, isoxazole, triazole or thiadiazole ring which is optionally substituted by (lower)alkyl, hydroxy, halogen or amino; and Ar is phenyl, optionally substituted by halogen, methyl or amino.

Belgian Pat. No. 844,504 (Farmdoc 07558Y) discloses $H_2$-receptor inhibitors of the formula

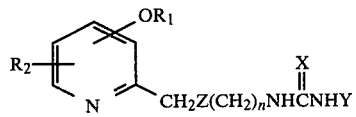

wherein $R_1$ is (lower)alkyl or —$(CH_2)_pA$; p is 2-4; A is hydroxy, (lower)alkoxy or dimethylamino; $R_2$ is hydrogen, (lower)alkyl, (lower)alkoxy, amino, methylamino or halogen; or —$OR_1$ and $R_2$ taken together form the group —$O(CH_2)_qO$— joined to two adjacent carbon atoms of the pyridine ring; q is 1-4; n is 2 or 3; Z is sulfur or —$CH_2$—; X is sulfur, $CHNO_2$, NH, NCN or NOH; and Y is inter alia hydrogen, (lower)alkyl or 2-hydroxyethyl.

U.S. Pat. No. 4,112,234 discloses histamine $H_2$-receptor inhibitors of the formula

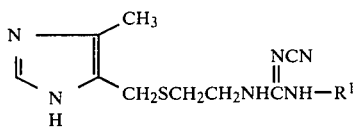

wherein $R^1$ is a straight or branched chain alkynyl group containing from 3 to 9 carbon atoms, and processes for the preparation thereof.

U.S. Pat. No. 4,060,621 discloses histamine $H_2$-receptor inhibitors of the formula

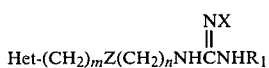

wherein Het is a pyridyl ring optionally substituted by (lower)alkyl, trifluoromethyl, hydroxyl, halogen or amino; Z is sulfur, oxygen, NH or a methylene group; m is 0, 1 or 2 and n is 2 or 3, the sum of m and n being from 2 to 4; X is $COR_3$, $CSR_3$, $SO_2R_4$, $NCHR_5$ or, when Z is methylene, may be nitro; $R_3$ is (lower)alkyl, (lower)alkoxy or, when Z is sulfur, oxygen or NH, may be amino; $R_4$ is (lower)alkyl, trifluoromethyl, amino or substituted or unsubstituted aryl, such as phenyl optionally substituted by halogen, (lower)alkyl or amino; $R_5$ is substituted or unsubstituted aryl, such as phenyl; and $R_1$ is hydrogen or (lower)alkyl such as methyl; and pharmaceutically acceptable salts thereof. U.S. Pat. No. 3,971,786 contains a substantially identical disclosure.

COMPLETE DISCLOSURE

This invention relates to histamine $H_2$-receptor antagonists which are effective inhibitors of gastric secretion in animals, including man, which are useful in the treatment of peptic ulcer disease and which have the formula

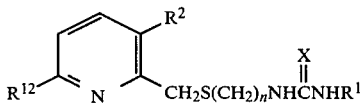

wherein $R^1$ is a straight or branched chain alkynyl group containing from 3 to 9 carbon atoms, inclusive; $R^2$ is hydrogen, hydroxy, cyano, (lower)alkyl, (lower)alkoxy, halogen or amino; n is 2 or 3; X is $NR^3$ or $CHR^3$; $R^3$ is cyano, nitro, $SO_2Ar$; or $SO_2$(lower)alkyl; $R^{12}$ is hydrogen or $(CH_2)_pNR^{13}R^{14}$; p is an integer of from 1 to 4, inclusive; $R^{13}$ and $R^{14}$ each are independently hydrogen or (lower)alkyl; and Ar is phenyl or phenyl containing 1 or 2 substituents independently selected from halogen and (lower)alkyl; and nontoxic, pharmaceutically acceptable salts thereof.

A preferred embodiment of the invention is a compound of the formula

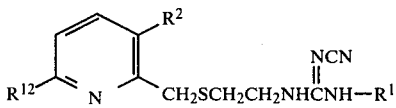

wherein $R^1$, $R^2$ and $R^{12}$ are as defined above, or a nontoxic, pharmaceutically acceptable salt thereof.

Another preferred embodiment of the invention is a compound of the formula

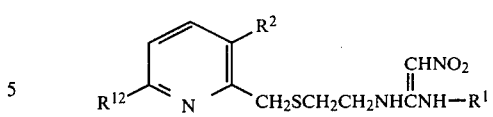

wherein $R^1$, $R^2$ and $R^{12}$ are as defined above, or a nontoxic, pharmaceutically acceptable salt thereof.

Another preferred embodiment of the invention is a compound of the formula

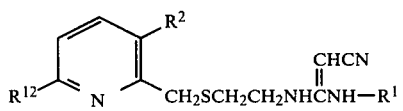

wherein $R^1$, $R^2$ and $R^{12}$ are as defined above, or a nontoxic, pharmaceutically acceptable salt thereof.

Another preferred embodiment of the invention is a compound of the formula

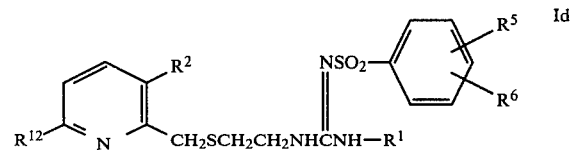

wherein $R^1$, $R^2$ and $R^{12}$ are as defined above; and $R^5$ and $R^6$ are independently selected from hydrogen, halogen and (lower)alkyl; or a nontoxic, pharmaceutically acceptable salt thereof.

Another preferred embodiment of the invention is a compound of the formula

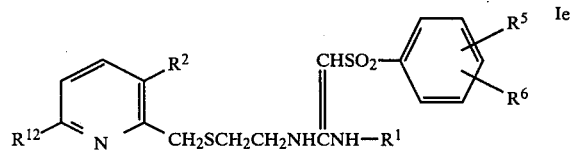

wherein $R^1$, $R^2$ and $R^{12}$ are as defined above; and $R^5$ and $R^6$ are independently selected from hydrogen, halogen and (lower)alkyl; or a nontoxic, pharmaceutically acceptable salt thereof.

A more preferred embodiment of the invention is a compound of the formula

wherein $R^2$ is as defined above; m is an integer of from 1 to 6, inclusive; and $R^7$ is hydrogen or methyl; or a nontoxic, pharmaceutically acceptable salt thereof.

Another more preferred embodiment of the invention is a compound of the formula

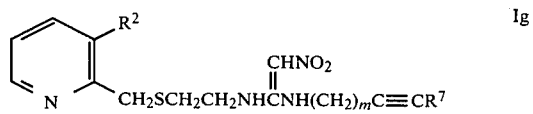

wherein $R^2$ is as defined above; m is an integer of from 1 to 6, inclusive; and $R^7$ is hydrogen or methyl; or a nontoxic, pharmaceutically acceptable salt thereof.

Another more preferred embodiment of the invention is a compound of the formula

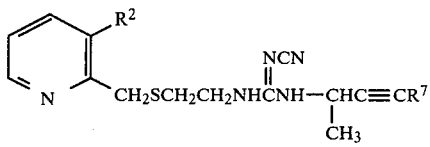

Ih wherein $R^2$ and $R^7$ are as defined above, or a nontoxic, pharmaceutically acceptable salt thereof.

Another more preferred embodiment of the invention is a compound of the formula

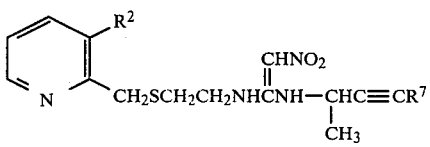

Ii wherein $R^2$ and $R^7$ are as defined above, or a nontoxic, pharmaceutically acceptable salt thereof.

Another more preferred embodiment of the invention is a compound of the formula

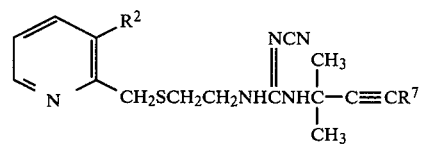

Ij wherein $R^2$ and $R^7$ are as described above, or a nontoxic, pharmaceutically acceptable salt thereof.

Another more preferred embodiment of the invention is a compound of the formula

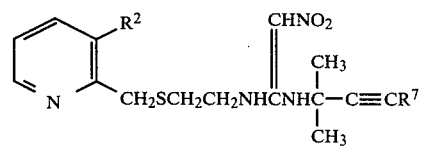

Ik wherein $R^2$ and $R^7$ are as described above, or a nontoxic, pharmaceutically acceptable salt thereof.

A still more preferred embodiment of the invention is a compound of the formula

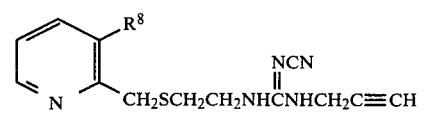

Im wherein $R^8$ is hydrogen, halogen or (lower)alkyl, or a nontoxic, pharmaceutically acceptable salt thereof.

Another still more preferred embodiment of the invention is a compound of the formula

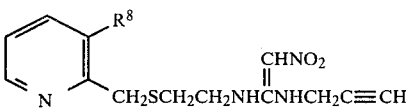

In wherein $R^8$ is hydrogen, halogen or (lower)alkyl, or a nontoxic, pharmaceutically acceptable salt thereof.

An even more preferred embodiment of the invention is 1-nitro-2-(2-propynylamino)-2-{2-[(2-pyridyl)methylthio]-ethylamino}ethylene or a nontoxic, pharmaceutically acceptable salt thereof.

Another even more preferred embodiment of the invention is N-cyano-N'-(2-propyn-1-yl)-N''-{2-[(2-pyridyl)methylthio]-ethyl}guanidine or a nontoxic pharmaceutically acceptable salt thereof.

A most preferred embodiment of the invention is 1-nitro-2-(2-propynylamino)-2-{2-[(3-chloro-2-pyridyl)-methylthio]ethylamino}ethylene or a nontoxic, pharmaceutically acceptable salt thereof.

Another most preferred embodiment of the invention is N-cyano-N'-(2-propyn-1-yl)-N''-{2-[(3-chloro-2-pyridyl)-methylthio]ethyl}guanidine or a nontoxic, pharmaceutically acceptable salt thereof.

Although the compounds of this invention have been shown as having the structure of Formula I, it will be appreciated by those skilled in the art that the compounds in which X is $CHR^3$ can exist in various tautomeric forms, as follows:

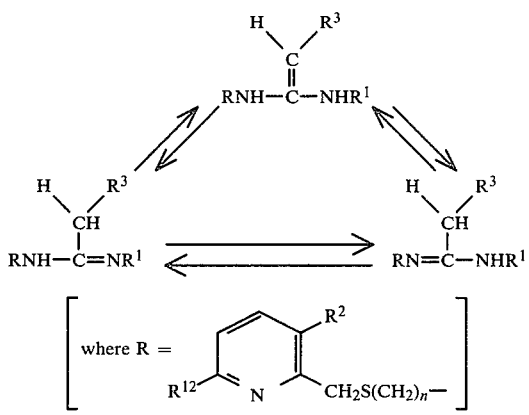

Also, the compounds in which X is $CHR^3$ may exist as two geometric isomers, i.e., cis/trans isomers about the double bond. In addition, all the compounds of Formula I which contain a branched chain alkynyl group as substituent $R^1$ may exist as their d- or l-optical isomers as well as their racemic forms. Thus, for example 3-amino-1-butyne of the formula

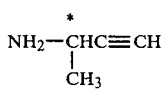

may be resolved into its d- and l-isomers as described by A. Marszak-Fleury, Compt. rend., 242, 1046 (1956). The use of the d- or l-isomer of the alkynylamine in the preparation of a compound of Formula I produces the corresponding d- or l-isomer of the compound of Formula I. The present invention includes within its scope all possible tautomeric forms, geometric isomers and optical isomers of the compounds of Formula I as well as mixtures thereof.

The compounds of the present invention may be prepared by various alternative reaction schemes, as illustrated below for two embodiments of the invention, compounds Io and Ip.

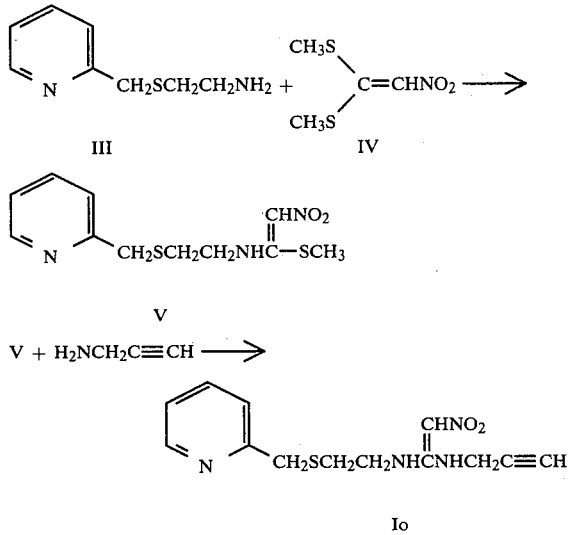

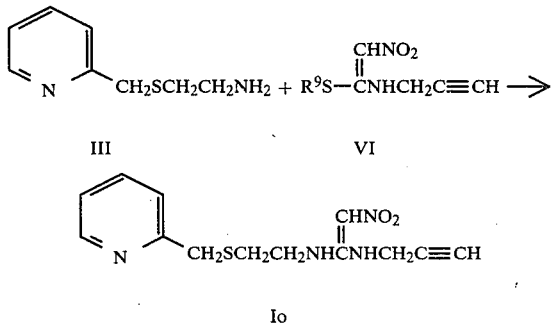

The compound of Formula III is prepared by the procedure described in U.S. Pat. No. 3,905,984. Analogous and homologous compounds are prepared by procedures described in U.S. Pat. Nos. 3,905,984, 3,876,647 and 4,024,260, or by analogous procedures. The compound of Formula IV is prepared by procedures described in *Chem. Ber.*, 100, 591 (1967) or *Acta Chem. Scand.*, 21, 2797 (1967). The reaction steps of Scheme I are conducted in a non-reactive solvent such as isopropyl alcohol at or above room temperature. The alkynylamines utilized as starting materials (propargylamine illustrated above) are either commercially available or may be prepared by procedures described in *Bull. Soc. Chim. Fr.*, 490 (1958), *Bull. Soc. Chim. Fr.*, 588 (1967), *Bull. Soc. Chim. Fr.*, 592 (1967), *Annales de Chimie* (Paris), 3, 656 (1958) and *J. Org. Chem.*, 21, 791 (1956).

The reaction is conducted in a non-reactive solvent such as methanol at or above room temperature. As will be appreciated by those skilled in the art, $R^9$ may be any substituent such that $-SR^9$ will be a suitable leaving group. Such leaving groups are conventional in the art. Thus, $R^9$ may be (lower)alkyl, aryl or substituted aryl (e.g. p-nitrophenyl), or the like. The compounds of Formula VI may themselves be prepared by alternative procedures, such as illustrated below for the preparation of Compound VI wherein $R^9$ is methyl.

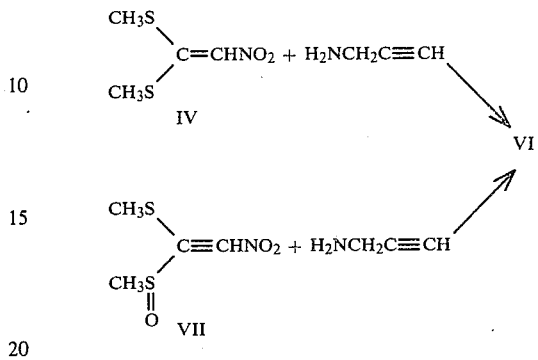

The compound of Formula VII is prepared by the procedures described in Belgian Pat. No. 841,526 and analogous compounds may be prepared by analogous procedures. It will be apparent to those skilled in the art that, if the propargylamine utilized above is replaced by a different alkynylamine, there will be produced a compound of Formula VI which contains the different alkynyl group. That compound, in turn, can be reacted with a compound of Formula III to produce a compound of Formula I containing the different alkynyl group.

Scheme III

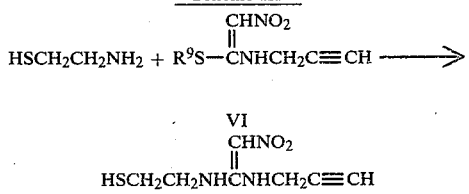

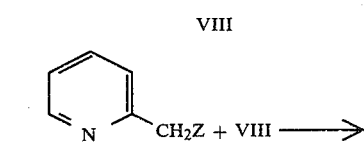

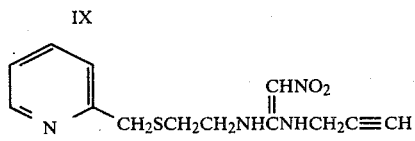

The reaction steps are conducted in a non-reactive solvent at or above room temperature. Compound VI is prepared as described above in Scheme II. Substituent Z in Compound IX is a conventional leaving group. Suitable leaving groups "Z" for use in this reaction are well-known to those skilled in the art. They include, for example, fluoro, chloro, bromo, iodo, $-O_3SR^{10}$ wherein $R^{10}$ is (lower)alkyl [e.g. methanesulfonate], $-O_3SR^{11}$ wherein $R^{11}$ is aryl or substituted aryl [e.g. benzenesulfonate, p-bromobenzenesulfonate or p-toluenesulfonate], $-O_3SF$, acetoxy and 2,4-dinitrophenoxy. For convenience and economy we normally prefer to utilize compound IX in which Z is chloro. The compound of Formula IX, and analogous compounds, are either commercially available or may be prepared by general procedures described in Belgian Pat. Nos. 779,775, 804,144, 814,941 or 844,504.

Scheme IV

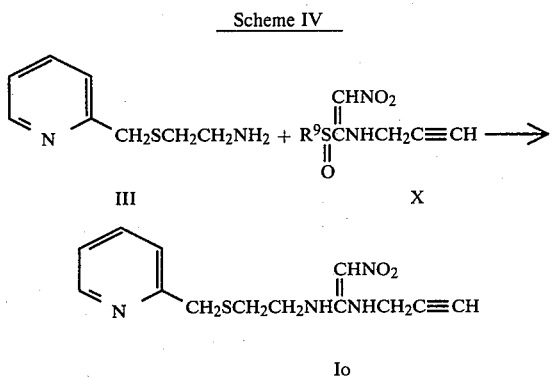

Io

The reaction is conducted in a non-reactive solvent at or above room temperature. The compound of Formula X, in which $R^9$ is as described above, is prepared by oxidation of a compound of Formula VI by conventional means.

Scheme V

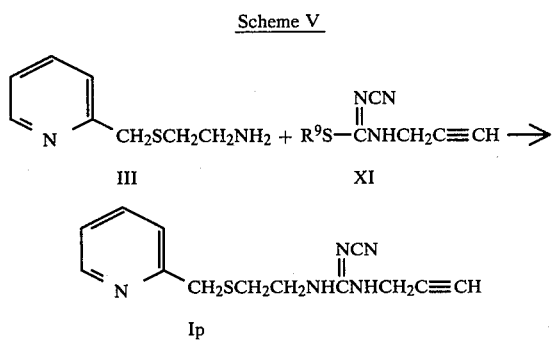

Ip

The reaction is conducted in a non-reactive solvent at or above room temperature. The compounds of Formula XI may be prepared by procedures described by our colleagues U.S. patent application Ser. No. 936,668, filed Aug. 24, 1978, the complete disclosure of which is incorporated herein by reference. For example, Compound XI in which $R^9$ is methyl may be prepared by reacting dimethyl cyanodithioimidocarbonate with propargylamine. The dimethyl cyanodithioimidocarbonate may itself be prepared by procedures described in *J. Org. Chem.*, 32, 1566 (1967). Analogous compounds may be prepared by analogous procedures.

Scheme VI

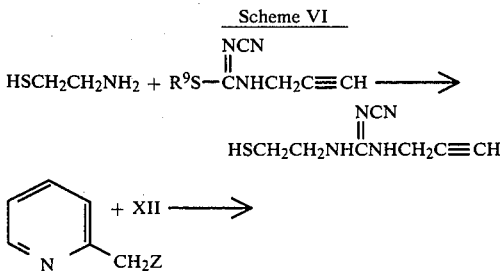

-continued
Scheme VI

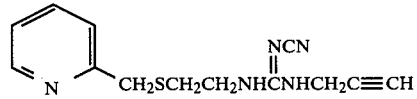

Ip

The reaction, which is analogous to that described in Scheme III above, is conducted in a non-reactive solvent at or above room temperature. The compound of Formula XII and homologous and analogous compounds containing other alkynyl groups are described and claimed in our colleagues U.S. patent application Ser. No. 906,901, filed May 18, 1978, the complete disclosure of which is incorporated herein by reference.

Scheme VII

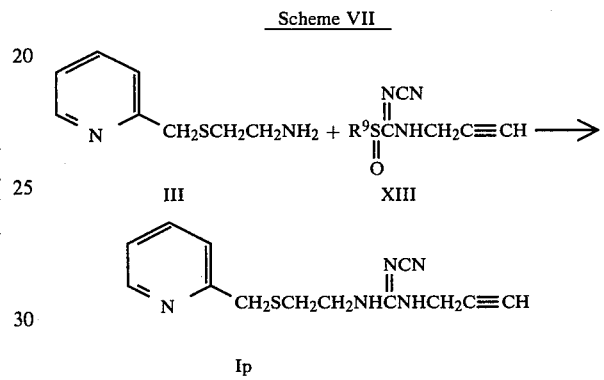

Ip

The reaction, which is analogous to that described in Scheme IV above, is conducted in a non-reactive solvent at or above room temperature. The compounds of Formula XIII are prepared by oxidation of a compound of Formula XI by conventional means.

Scheme VIII

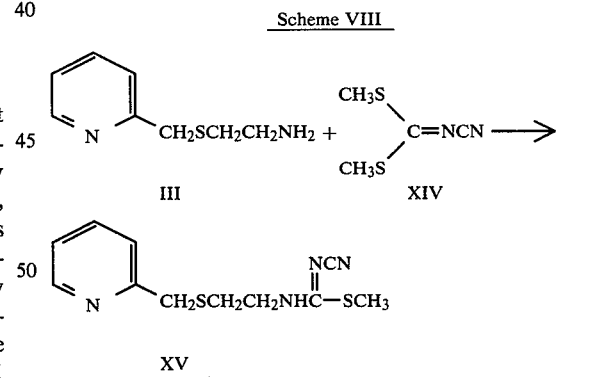

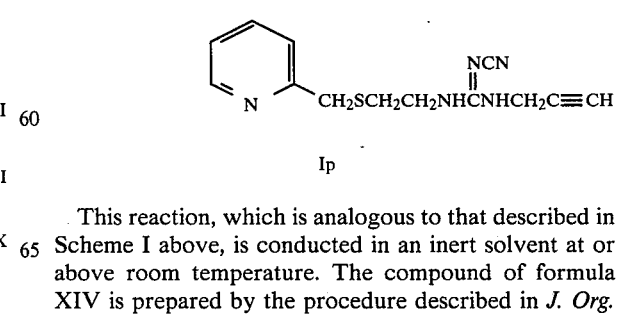

Ip

This reaction, which is analogous to that described in Scheme I above, is conducted in an inert solvent at or above room temperature. The compound of formula XIV is prepared by the procedure described in *J. Org. Chem.*, 32, 1566 (1967). The compound of formula XV (and its analogs) is itself disclosed in Belgian Pat. No. 804,144.

As used herein, the term nontoxic pharmaceutically acceptable acid addition salt means the mono- or di-salt of a compound of this invention with a nontoxic pharmaceutically acceptable organic or inorganic acid. Such acids are well known and include hydrochloric, hydrobromic, sulfuric, sulfamic, phosphoric, nitric, maleic, fumaric succinic, oxalic, benzoic, methanesulfonic, ethanedisulfonic, benzenesulfonic, acetic, propionic, tartaric, citric, camphorsulfonic, and the like. The salts are made by methods known in the art.

The term "(lower)alkyl," as used herein, means a straight or branched chain alkyl group containing from 1 to 6 carbon atoms. Similarly, the term "(lower)alkoxy" means an alkoxy group in which the alkyl portion is straight or branched and contains from 1 to 6 carbon atoms.

For therapeutic use, the pharmacologically active compounds of this invention will normally be administered as a pharmaceutical composition comprising as the (or an) essential active ingredient at least one such compound in the basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or non aqueous liquid suspension. The pharmaceutical compositions are prepared by conventional techniques appropriate to the desired preparation.

Preferably, each dosage unit will contain the active ingredient in an amount of from about 50 mg. to about 250 mg., and most preferably from about 100 mg. to about 200 mg. The active ingredient will preferably be administered in equal doses from two to four times a day. The daily dosage regimen will preferably be from 250 mg. to about 1000 mg., and most preferably from about 500 mg. to about 750 mg.

Histamine $H_2$-receptor antagonists have been shown to be effective inhibitors of gastric secretion in animals and man, Brimblecombe et al., *J. Int. Med. Res.*, 3, 86 (1975). Clinical evaluation of the histamine $H_2$-receptor antagonist cimetidine has shown it to be an effective therapeutic agent in the treatment of peptic ulcer disease, Gray et al., *Lancet*, 1 (8001), 4 (1977). The compounds prepared in Examples 19 (BL-6075) and 20 (BL-6083) below have been found to be 2.09 times and 8.19 times, respectively, more potent than cimetidine as a histamine $H_2$-receptor antagonist in isolated guinea pig atria.

HISTAMINE $H_2$-RECEPTOR ANTAGONISM-ISOLATED GUINEA PIG ATRIA ASSAY

Histamine produces concentration-related increases in the contractile rate of isolated, spontaneously beating guinea pig right atria. Black et al., *Nature*, 236, 385 (1972), described the receptors involved in this effect of histamine as histamine $H_2$-receptors when they reported the properties of burimamide, a competitive antagonist of these receptors. Subsequent investigations by Hughes and Coret, *Proc. Soc. Exp. Biol. Med.*, 148, 127 (1975) and Verma and McNeill, *J. Pharmacol. Exp. Ther.*, 200, 352 (1977) support the conclusion of Black and coworkers that the positive chronotropic effect of histamine in isolated guinea pig right atria is mediated via histamine $H_2$-receptors. Black et al., *Agents and Actions*, 3, 133 (1973) and Brimblecombe et al., *Fed. Proc.*, 35, 1931 (1976) have utilized isolated guinea pig right atria as a means for comparing the activities of histamine $H_2$-receptor antagonists. The present comparative studies were carried out using a modification of the procedure reported by Reinhardt et al., *Agents and Actions*, 4, 217 (1974).

Male Hartley strain guinea pigs (350-450 gm.) were sacrificed by a blow on the head. The heart was excised and placed in a Petri dish of oxygenated (95% $O_2$, 5% $CO_2$) modified Krebs solution (g./liter: NaCl 6.6, KCl 0.35, $MgSO_4.7H_2O$ 0.295, $KH_2PO_4$ 0.162, $CaCl_2$ 0.238, $NaHCO_3$ 2.1 and dextrose 2.09). The spontaneously beating right atrium was dissected free from other tissues and a silk thread (4-0) attached to each end. The atrium was suspended in a 20 ml. muscle chamber containing oxygenated modified Krebs solution maintained at 32° C. Atrial contractions were recorded isometrically be means of a Grass FT 0.03 force displacement transducer and recordings of contractile force and rate were made with Beckman RP Dynograph.

A resting tension of 1 g. was applied to the atrium and it was allowed to equilibrate for 1 hour. At the end of the equilibration period a submaximal concentration of histamine dihydrochloride ($3 \times 10^{-6}$ M) was added to the bath and washed out to prime the tissue. Histamine was then added to the bath in a cumulative fashion using ½ log 10 intervals to give final molar bath concentrations of $1 \times 10^{-7}$ to $3 \times 10^{-5}$. The histamine-induced increase in atrial rate was allowed to plateau before the next successive concentration was added. The maximal response invariably occurred at the $3 \times 10^{-5}$ M concentration. The histamine was washed out several times and the atrium allowed to return to control rate. The test compound ($3 \times 10^{-5}$ M) was then added and after a 30 minute incubation the histamine concentration-response was repeated adding higher concentrations as needed.

The histamine ED50 values (concentration of histamine which increased contractile rate 50% of maximum) and 95% confidence limits before and after the test compound were obtained by regression analysis as described by Finney, *Probit Analysis*, 3rd ed., Cambridge (1971). Concentration-response curve displacement factors were calculated as follows:

$$\text{Displacement factor} = \frac{\text{ED50 Histamine + Compound}}{\text{ED50 Histamine Alone}}$$

The factors obtained for BL-6075 and BL-6083 were then expressed as ratios of the factor obtained for cimetidine.

$$\text{Activity Ratio} = \frac{\text{Test Compound Displacement Factor - 1}}{\text{Cimetidine Displacement Factor - 1}}$$

The results obtained from these studies are summarized in Table 1. Cimetidine, BL-6075 and BL-6083 displaced the histamine concentration-response curve to the right by factors of 25.26, 52.77 and 206.86, respectively. Based on the concentration-response curve displacement of factors, BL-6075 and BL-6083 were about 2.09 times and 8.19 times, respectively, more active than cimetidine as a histamine $H_2$-receptor antagonist in isolated guinea pig right atria.

TABLE 1

Relative Activity of Cimetidine, BL-6075 and BL-6083 in Isolated Guniea Pig Right Atria

| Compound | N | Concentration | Histamine ED50 With 95% Confidence Limits (μg/ml) | Concentration-Response Curve Displacement Factor | Activity Ratio Relative to Cimetidine |
|---|---|---|---|---|---|
| Histamine control | 8 | — | 0.19 (0.15–0.24) | — | — |
| Cimetidine | 8 | $3 \times 10^{-5}M$ | 4.80 (3.9–5.9) | 25.26 | 1.0 |
| Histamine control | 3 | — | 0.39 (0.28–0.52) | — | — |
| BL-6075 | 3 | $3 \times 10^{-5}M$ | 20.97 (16.03–27.85) | 52.77 | 2.09 |
| Histamine control | 5 | — | 0.28 (0.21–0.84) | — | — |
| BL-6083 | 5 | $3 \times 10^{-5}M$ | 57.92 (48.5–69.8) | 206.86 | 8.19 |

N = Number of experiments.

EXAMPLE 1

1-Nitro-2-(propynylamino)-2-{2-[(2-pyridyl)methylthio]-ethylamino}ethylene (BL-6023)

A.

1-Nitro-2-methylthio-2-{2-[(2-pyridyl)methylthio]-ethylamino}ethylene

A solution of 2-[(2-pyridyl)methylthio]ethylamine (from the dihydrobromide, 20.0 g; 60.6 mmoles) [prepared according to the procedure described in Belgian Pat. No. 779,775] and 1,1-bis(methylthio)-2-nitroethylene [prepared according to the procedure described in *Chem. Ber.*, 100, 591 (1967) or *Acta Chem. Scand.*, 21, 2797 (1967)] (10.0 g; 60.6 mmoles) in isopropyl alcohol (175 ml) was stirred at ambient temperature under a positive pressure of nitrogen for 16 hours then at reflux temperature for 2 hours to complete the reaction. The mixture was cooled in an ice-water bath and the product collected by filtration. Recrystallization from isopropyl alcohol with activated carbon treatment gave 1-nitro-2-methylthio-2-{2-[(2-pyridyl)methylthio]-ethylamino}ethylene; mp 97°–99°.

B.

1-Nitro-2-(propynylamino)-2-{2-[(2-pyridyl)methylthio]-ethylamino}ethylene

A mixture of the product of Step A (2.0 g; 7.03 mmoles and propargylamine (3.44 g; 62.5 mmoles) in acetonitrile (30 ml) was stirred and heated to reflux temperature under a positive pressure of nitrogen for 1.5 hours then stirred at ambient temperature for 42 hours. The reaction mixture was filtered and the product collected. Recrystallization from acetonitrile gave the title compound; mp 147°–148°.

Anal. Calcd for $C_{13}H_{16}N_4O_2S$: C, 53.40; H, 5.52; N, 19.16; S, 10.97. Found: C, 53.52; H, 5.50; N, 19.30; S, 10.83.

EXAMPLE 2

1-Nitro-2-(propynylamino)-2-{2-[(2-pyridyl)methylthio]-ethylamino}ethylene (BL-6023)

A. 1-Methylthio-1-(2-propynylamino)-2-nitroethylene

A solution of propargylamine (1.10 g, 0.02 mole) in 22 ml of methanol was added dropwise to a stirred suspension of 1-methylsulfinyl-1-methylthio-2-nitroethylene [prepared according to the procedure described in Belgian Pat. No. 841,526] at 25°. After 1 hour at ambient temperature, the solution was evaporated under reduced pressure, triturated under 20 ml of cold isopropyl alcohol and filtered to give product. Recrystallization from isopropyl alcohol gave 1-methylthio-1-(2-propynylamino)-2-nitroethylene; mp 131°–132°.

B.

1-Nitro-2-(propynylamino)-2-{2-[(2-pyridyl)methylthio]-ethylamino}ethylene

A solution of the product of Step A is treated with about an equimolar amount of 2-[(2-pyridyl)methylthio]-ethylamine to produce, after workup, the title product.

EXAMPLE 3

1-Nitro-2-(propynylamino)-2-{2-[(2-pyridyl)methylthio]-ethylamino}ethylene (BL-6023)

A.

1-Nitro-2-(2-propynylamino)-2-(2-mercaptoethyl)ethylene

A solution of the product of Step A of Example 2 is reacted with about an equimolar amount of cysteamine hydrochloride and about two equivalents of base, and the title product is produced.

B.

1-Nitro-2-(propynylamino)-2-{2-[(2-pyridyl)methylthio]-ethylamino}ethylene

The product of Step A is reacted in a non-reactive solvent with about an equimolar amount of 2-chloromethylpyridine hydrochloride and about one equivalent of base, and the title product is thereby produced.

EXAMPLE 4

N-Cyano-N'-(2-propyn-1-yl)-N''-{2-[(2-pyridyl)methylthio]-ethyl}guanidine (BL-6043)

A.

N-Cyano-N'-{2-[(2-pyridyl)methylthio]ethyl}-S-methylisothiourea

A solution of 2-[(2-pyridyl)methylthio]ethylamine (from the dihydrobromide, 20.0 g; 60.6 mmoles) and dimethyl cyanodithioimidocarbonate [prepared according to the procedure described in *J. Org. Chem.*, 32, 1566 (1967)] (8.86 g; 60.6 mmoles) in methanol (150 ml) was stirred at ambient temperature under a positive pressure of nitrogen for 16 hours and then a reflux temperature for 0.5 hours to complete the reaction. The reaction mixture was evaporated under reduced pressure and the crude product was recrystallized from acetonitrile to give N-cyano-N'-{2-[(2-pyridyl)methylthio]-ethyl}-S-methylisothiourea; mp 85°–86.5° C.

B.
N-Cyano-N'-(2-propyn-1-yl)-N''-{2-[(2-pyridyl)methylthio]-ethyl}guanidine

A mixture of the product of Step A (4.0 g; 15.0 mmoles) and propargylamine (6.88 g; 125 mmoles) in methanol (20 ml) was stirred and heated to reflux temperature under a positive pressure of nitrogen for 20 hours. The reaction mixture was evaporated under reduced pressure and the product recrystallized from acetonitrile to give the title compound; mp 124.5°–130.5° C. (remelted at 128°–131.5° C.).

Anal. Calcd for $C_{13}H_{15}N_5S$: C, 57.12; H, 5.53; N, 25.62; S, 11.73. Found: C, 57.29; H, 5.28; N, 25.78; S, 11.54.

EXAMPLE 5

N-Cyano-N'-(2-propyn-1-yl)-N''-{2-[(2-pyridyl)methylthio]-ethyl}guanidine (BL-6043)

A. N-Cyano-N'-(2-propyn-1-yl)-S-methylisothiourea

A solution of dimethyl cyanodithioimidocarbonate (16.0 g; 0.109 mole) and propargylamine (6.03 g; 0.109 mole) in acetonitrile (320 ml) was stirred at reflux for 4 hours, then at ambient temperature for 12 hours. Workup gave 13.58 g (85%) of N-cyano-N'-(2-propyn-1-yl)-S-methylisothiourea; mp 160°–164°.

B.
N-Cyano-N'-(2-propyn-1-yl)-N''-{2-[(2-pyridyl)methylthio]-ethyl}guanidine

The product of Step A is reacted with about an equimolar amount of 2-[(2-pyridyl)methylthio]ethylamine in a nonreactive solvent to give after workup, the title product.

EXAMPLE 6

N-Cyano-N'-(2-propyn-1-yl)-N''-{2-[(2-pyridyl)methylthio]-ethyl}guanidine (BL-6043)

A.
N-Cyano-N'-(2-propyn-1-yl)-N''-(2-mercaptoethyl)-guanidine

A mixture of the product of Step A of Example 5 (1.53 g; 10 mmoles), cysteamine hydrochloride (1.136 g; 10 mmoles) and 0.055 g of hydroquinone in 10 ml of dimethylformamide is slightly warmed to dissolve. To this solution is added 10 ml of 1 N aqueous sodium hydroxide and nitrogen is bubbled through the solution. After standing at room temperature for 17 hours, the reaction mixture is evaporated to dryness to give a mixture of the title compound and sodium chloride. The title compound is extracted from the mixture with 10 ml of ethanol and the ethanolic solution is used in Step B below.

B.
N-Cyano-N'-(2-propyn-1-yl)-N''-{2-[(2-pyridyl)methylthio]-ethyl}guanidine

The ethanolic solution of the product of Step A is reacted with about an equimolar amount of 2-chloromethylpyridine hydrochloride and about two equivalents of base to produce the title product.

EXAMPLE 7

The general procedure of Example 1 is repeated except that the propargylamine utilized therein is replaced by an equimolar amount of
2-butyn-1-amine,
3-butyn-1-amine,
4-pentyn-1-amine,
3-amino-1-butyne and
1,1-dimethylpropargylamine, respectively,
and there is thereby produced
1-nitro-2-(2-butyn-1-ylamino)-2-{2-[(2-pyridyl)methylthio]-ethylamino}ethylene,
1-nitro-2-(3-butyn-1-ylamino)-2-{2-[(2-pyridyl)methylthio]-ethylamino}ethylene,
1-nitro-2-(4-pentyn-1-ylamino)-2-{2-[(2-pyridyl)methylthio]-ethylamino}ethylene,
1-nitro-2-(3-butyn-2-ylamino)-2-}2-[(2-pyridyl)methylthio]-ethylamino}ethylene and
1-nitro-2-(2-methyl-3-butyn-2-ylamino)-2-{2-[(2-pyridyl)-methylthio]ethylamino}ethylene, respectively.

EXAMPLE 8

The general procedure of Example 4 is repeated except that the propargylamine utilized therein is replaced by an equimolar amount of
2-butyn-1-amine,
3-butyn-1-amine,
4-pentyn-1-amine,
3-amino-1-butyne and
1,1-dimethylpropargylamine, respectively,
and there is thereby produced
N-cyano-N'-(2-butyn-1-yl)-N''-{2-[(2-pyridyl)methylthio]-ethyl}guanidine,
N-cyano-N'-(3-butyn-1-yl)-N''-{2-[(2-pyridyl)methylthio]-ethyl}guanidine,
N-cyano-N'-(4-pentyn-1-yl)-N''-{2-[(2-pyridyl)methylthio]-ethyl}guanidine,
N-cyano-N'-(3-butyn-2-yl)-N''-{2-[(2-pyridyl)methylthio]-ethyl}guanidine and
N-cyano-N'-(2-methyl-3-butyn-2-yl)-N''-{2-[(2-pyridyl)-methylthio]ethyl}guanidine, respectively.

EXAMPLE 9

The general procedure of Example 1 is repeated except that the 2-[(2-pyridyl)methylthio]ethylamine utilized therein is replaced by an equimolar amount of
2-[(3-bromo-2-pyridyl)methylthio]ethylamine,
2-[(3-cyano-2-pyridyl)methylthio]ethylamine,
2-[(3-hydroxy-2-pyridyl)methylthio]ethylamine,
2-[(3-methoxy-2-pyridyl)methylthio]ethylamine,
2-[(3-ethoxy-2-pyridyl)methylthio]ethylamine,
2-[(3-methyl-2-pyridyl)methylthio]ethylamine and
2-[(3-amino-2-pyridyl)methylthio]ethylamine, respectively,
and there is thereby produced
1-nitro-2-(2-propynylamino)-2-{2-[(3-bromo-2-pyridyl)-methylthio]ethylamino}ethylene,
1-nitro-2-(2-propynylamino)-2-{2-[(3-cyano-2-pyridyl)-methylthio]ethylamino}ethylene,
1-nitro-2-(2-propynylamino)-2-{2-[(3-hydroxy-2-pyridyl)-methylthio]ethylamino}ethylene,
1-nitro-2-(2-propynylamino)-2-{2-[(3-methoxy-2-pyridyl)-methylthio]ethylamino}ethylene, 1-nitro-2-(2-propynylamino)-2-{2-[(3-ethoxy-2-pyridyl)-methylthio]ethylamino}ethylene,
1-nitro-2-(2-propynylamino)-2-{2-[(3-methyl-2-pyridyl)-methylthio]ethylamino}ethylene and
1-nitro-2-(2-propynylamino)-2-{2-[(3-amino-2-pyridyl)-methylthio]ethylamino}ethylene, respectively.

The starting materials utilized herein may be prepared according to general procedures described in Belgian Pat. Nos. 779,775, 804,144 and 844,504.

EXAMPLE 10

The general procedure of Example 4 is repeated except that the 2-[(2-pyridyl)methylthio]ethylamine utilized therein is replaced by an equimolar amount of
2-[(3-bromo-2-pyridyl)methylthio]ethylamine,
2-[(3-cyano-2-pyridyl)methylthio]ethylamine,
2-[(3-hydroxy-2-pyridyl)methylthio]ethylamine,
2-[(3-methoxy-2-pyridyl)methylthio]ethylamine,
2-[(3-ethoxy-2-pyridyl)methylthio]ethylamine,
2-[(3-methyl-2-pyridyl)methylthio]ethylamine and
2-[(3-amino-2-pyridyl)methylthio]ethylamine, respectively,
and there is thereby produced
N-cyano-N'-(2-propyn-1-yl)-N''-{2-[(3-bromo-2-pyridyl)-methylthio]ethyl}guanidine,
N-cyano-N'-(2-propyn-1-yl)-N''-{2-[(3-cyano-2-pyridyl)-methylthio]ethyl}guanidine,
N-cyano-N'-(2-propyn-1-yl)-N''-{2-[(3-hydroxy-2-pyridyl)-methylthio]ethyl}guanidine,
N-cyano-N'-(2-propyn-1-yl)-N''-{2-[(3-methoxy-2-pyridyl)-methylthio]ethyl}guanidine,
N-cyano-N'-(2-propyn-1-yl)-N''-{2-[(3-ethoxy-2-pyridyl)-methylthio]ethyl}guanidine,
N-cyano-N'-(2-propyn-1-yl)-N''-{2-[(3-methyl-2-pyridyl)-methylthio]ethyl}guandine and
N-cyano-N'-(2-propyn-1-yl)-N''-{2-[(3-amino-2-pyridyl)-methylthio]ethyl}guanidine, respectively.

EXAMPLE 11

1-Nitro-2-(2-propynylamino)-2-{3-[(3-chloro-2-pyridyl)-methylthio]propylamino}ethylene When 3-chloro-2-hydroxymethylpryridine is reacted with 3-mercaptopropylamine hydrochloride [prepared according to the procedure described in *J. Org. Chem.*, 27, 2846 (1962)] in aqueous hydrobromic acid (48%) and the resultant amine successively treated with 1,1-bis(methylthio)-2-nitroethylene and excess propargylamine according to the general procedure of Example 1, the title compound is produced.

EXAMPLE 12

N-Cyano-N'-(2-propyn-1-yl)-N''-{3-[(3-chloro-2-pyridyl)-methylthio]propyl}guanidine Reaction of 3-[(3-chloro-2-pyridyl)methylthio]-propylamine with dimethyl cyanodithioimidocarbonate and treatment of the resultant product with propargylamine according to the general procedure of Example 4 gives the title compound.

EXAMPLE 13

N-Phenylsulfonyl-N'-(2-propyn-1-yl)-N''-{2-[(3-chloro-2-pyridyl)methylthio]ethyl}guanidine Reaction of N-phenylsulfonylimidodithiocarbonic acid dimethyl ester [prepared according to the procedure described in U.K. Pat. No. 1,398,426] with 2-[(3-chloro-2-pyridyl)methylthio]ethylamine and then with excess propargylamine according to the procedure of Example 4 produces N-phenylsulfonyl-N'-(2-propyn-1-yl)-N''-{2-[(3-chloro-2-pyridyl)methylthio]ethyl}guanidine.

EXAMPLE 14

The general procedure of Example 13 is repeated except that the N-phenylsulfonylimidodithiocarbonic acid dimethyl ester is replaced by
N-(4-chlorophenylsulfonyl)imidodithiocarbonic acid dimethyl ester,
N-(4-methylphenylsulfonyl)imidodithiocarbonic acid dimethyl ester,
N-(3,4-dichlorophenylsulfonyl)imidodithiocarbonic acid dimethyl ester and
N-(methylsulfonyl)imidodithiocarbonic acid dimethyl ester, respectively, [each prepared by the procedure described in *Chem. Ber.*, 99, 2885 (1966)] and there is thereby produced
N-(4-chlorophenylsulfonyl)-N'-(2-propyn-1-yl)-N''-{2-[(3-chloro-2-pyridyl)methylthio]ethyl}guanidine,
N-(4-methylphenylsulfonyl)-N'-(2-propyn-1-yl)-N''-{2-[(3-chloro-2-pyridyl)methylthio]ethyl}guanidine,
N-(3,4-dichlorophenylsulfonyl)-N'-(2-propyn-1-yl)-N''-{2-[(3-chloro-2-pyridyl)methylthio]ethyl}guanidine and
N-(methylsulfonyl)-N'-(2-propyn-1-yl)-N''-{2-[(3-chloro-2-pyridyl)methylthio]ethyl}guanidine, respectively.

EXAMPLE 15

1-Phenylsulfonyl-2-(2-propynylamino)-2-{2-[(3-bromo-2-pyridyl)methylthio]ethylamino}ethylene The reaction of methyl phenyl sulfone with carbon disulfide under strongly basic conditions and treatment with methyl iodide yields 1-phenylsulfonyl-2,2-bis(methylthio)ethylene, [a known compound, which is described in *Bull. Soc. Chim. Fr.*, 637 (1973)]. Reaction of the latter compound with 2-[(3-bromo-2-pyridyl)methylthio]ethylamine, and then with propargylamine according to the general procedure of Example 1, produces the title product.

EXAMPLE 16

The general procedure of Example 15 is repeated except that the methyl phenyl sulfone utilized therein is replaced by an equimolar amount of
4-chlorophenyl methyl sulfone,
3,4-dichlorophenyl methyl sulfone,
4-methylphenyl methyl sulfone and
dimethyl sulfone, respectively,
[each prepared by the general procedure described in U.S. Pat. No. 4,046,907 or in *Bull. Soc. Chim. Fr.*, 637 (1937)]and there is thereby produced
1-(4-chlorophenylsulfonyl)-2-(2-propynylamino)-2-{2-[(3-bromo-2-pyridyl)methylthio]ethylamino}ethylene,
1-(3,4-dichlorophenylsulfonyl)-2-(2-propynylamino)-2-{2-[(3-bromo-2-pyridyl)methylthio]ethylamino}ethylene,
1-(4-methylphenylsulfonyl)-2-(2-propynylamino)-2-{2-[(3-bromo-2-pyridyl)methylthio]ethylamino}ethylene and
1-(methylsulfonyl)-2-(2-propynylamino)-2-{2-[(3-bromo-2-pyridyl)methylthio]ethylamino}ethylene.

EXAMPLE 17

1-Cyano-2-(2-propynylamino)-2-{2-[(3-chloro-2-pyridyl)-methylthio]ethylamino}ethylene When 2-[(3-chloro-2-pyridyl)methylthio]ethylamine is reacted with 1-cyano-2-ethoxy-2-propynylaminoethylene [prepared from propargylamine and 1-cyano-2,2-bis(ethoxy)-ethylene, which is itself prepared according to the procedure described in *J. Am.. Chem. Soc.*, 71, 47 (1949)], the title product is produced.

EXAMPLE 18

1-Cyano-2-(2-propynylamino)-2-{2-[(3-chloro-2-pyridyl)-methylthio]ethylamino}ethylene When 2-[(3-chloro-2-pyridyl)methylthio]ethylamine is reacted with 1-cyano-2,2-bis(methoxy)ethylene and the resultant 1-cyano-2-methoxy-2-{2-[(3-chloro-2-pyridyl)-methylthio]ethylamino}ethylene is reacted with propargylamine according to the general procedure of Example 1 Step B the title compound is produced.

EXAMPLE 19

1-Nitro-2-(2-propynlamino)-2-{2-[(3-chloro-2-pyridyl)-methylthio]ethylamino}ethylene (BL-6075)

A solution of 1-nitro-2-methylthio-2-{2-[(3-chloro-2-pyridyl)methylthio]ethylamino}ethylene (0.61 g; 1.91 mmoles) [prepared according to the procedure described in U.S. Pat. No. 4,024,260] and propargylamine (1.72 g; 31.2 mmoles) in acetonitrile (15 ml) was stirred and heated to reflux temperature under a positive pressure of nitrogen for 7 hours then allowed to stand at ambient temperature for 16 hours. The reaction mixture was filtered and 346 mg of product collected. Recrystallization from methanol with activated carbon treatment gave the title compound; mp 171°–171.5°.

Anal. Calcd for $C_{13}H_{15}ClN_4O_2S$: C, 47.77; H, 4.63; N, 17.14; Cl, 10.85; S, 9.81. Found: C, 47.78; H, 4.78; N, 16.94; Cl, 10.98; S, 9.83.

EXAMPLE 20

N-Cyano-N'-(2-propyn-1-yl)-N''-{2-[(3-chloro-2-pyridyl)-methylthio]ethyl}guanidine (BL-6083)

A.

N-Cyano-N'-{2-[(3-chloro-2-pyridyl)methylthio]-ethyl}-S-methylisothiourea

A solution of 2-[(3-chloro-2-pyridyl)methylthio]-ethylamine (5.77 g; 28.44 mmoles) and dimethyl cyanodithioimidocarbonate [prepared according to the procedure described in *J. Org. Chem.,* 32, 1566 (1967)] (4.16 g; 28.44 mmoles) in methanol (50 ml) was stirred at ambient temperature under a positive pressure of nitrogen for 16 hours and then at reflux for 0.5 hours to complete the reaction. The reaction mixture was evaporated under reduced pressure and the crude product was recrystallized from isopropyl alcohol with activated carbon treatment to give N-cyano-N'-{2-[(3-chloro-2-pyridyl)methylthio]ethyl}-S-methylisothiourea; mp 119.5°–121°.

B.

N-Cyano-N'-(2-propyn-1-yl)-N''-{2-[(3-chloro-2-pyridyl)methylthio]ethyl}guanidine A mixture of the product of Step A (3.0 g; 10.0 mmoles) and propargylamine (5.16 g; 93.7 mmoles) in methanol (20 ml) was stirred and heated to reflux temperature under a positive pressure of nitrogen for 16 hours. The reaction mixture was evaporated under reduced pressure and the crude product was recrystallized from isopropyl alcohol with activated carbon treatment to give 2.07 g of the title compound; mp 115°–116°.

Anal. Calcd for $C_{13}H_{14}ClN_5S$: C, 50.72; H, 4.58; N, 22.75; Cl, 11.52; S, 10.42. Found: C, 50.46; H, 4.52; N, 22.71; Cl, 11.36; S, 10.55.

EXAMPLE 21

1-Nitro-2-(2-propynylamino)-2-{2-[(6-dimethylaminomethyl-2-pyridyl)methylthio]ethylamino}ethylene A solution of the product of Step A of Example 3 is reacted with about an equimolar amount of 6-dimethylaminomethyl-2-chloromethylpyridine hydrochloride (prepared from 2,6-dichloromethylpyridine hydrochloride and about two equivalents of dimethylamine) and about three equivalents of base, and the title product is produced.

EXAMPLE 22

N-Cyano-N'-(2-propyn-1-yl)-N''-{2-[(6-dimethylaminomethyl-2-pyridyl)methylthio]ethyl}guanidine A ethanolic solution of the product of Step A of Example 6 is reacted with about an equimolar amount of 6-dimethylaminomethyl-2-chloromethylpyridine hydrochloride and about three equivalents of base, and the title compound is produced.

We claim:

1. A compound of the formula

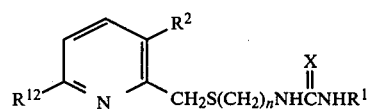

I wherein $R^1$ is a straight or branched chain alkynyl group containing from 3 to 9 carbon atoms, inclusive; $R^2$ is hydrogen, hydroxy, cyano, (lower)alkyl, (lower)alkoxy, halogen or amino; n is 2 or 3; X is $CHNO_2$; $R^{12}$ is hydrogen or $(CH_2)_pNR^{13}R^{14}$; p is an integer of from 1 to 4, inclusive; and $R^{13}$ and $R^{14}$ each are independently hydrogen or (lower)alkyl or a nontoxic, pharmaceutically acceptable salt thereof.

2. A compound of claim 1 having the formula

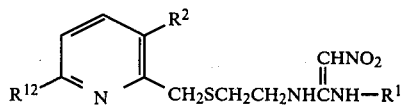

Ib wherein $R^1$, $R^2$ and $R^{12}$ are as defined in claim 1, or a nontoxic, pharmaceutically acceptable salt thereof.

3. A compound of claim 1 having the formula

Ig wherein $R^2$ is as defined in claim 1; m is an integer of from 1 to 6, inclusive; and $R^7$ is hydrogen or methyl; or a nontoxic, pharmaceutically acceptable salt thereof.

4. A compound of claim 1 having the formula

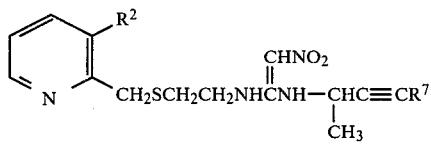

wherein $R^2$ is as defined in claim 1 and $R^7$ is hydrogen or methyl, or a nontoxic, pharmaceutically acceptable salt thereof.

5. A compound of claim 1 having the formula

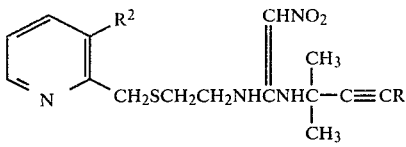

wherein $R^2$ is as defined in claim 1 and $R^7$ is hydrogen or methyl, or a nontoxic, pharmaceutically acceptable salt thereof.

6. A compound of the formula

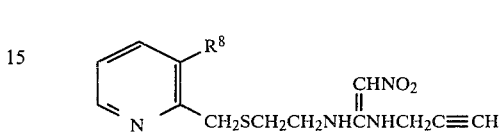

wherein $R^8$ is hydrogen, halogen or (lower)alkyl, or a nontoxic, pharmaceutically acceptable salt thereof.

7. 1-Nitro-2-(2-propynylamino)-2-{2-[(2-pyridyl)methylthio]ethylamino}ethylene or a nontoxic, pharmaceutically acceptable salt thereof.

8. 1-Nitro-2-(2-propynylamino)-2-{2-[(3-chloro-2-pyridyl)methylthio]ethylamino}ethylene or a nontoxic, pharmaceutically acceptable salt thereof.

* * * * *